(12) United States Patent
Roersma et al.

(10) Patent No.: US 10,518,106 B2
(45) Date of Patent: Dec. 31, 2019

(54) DEVICE AND METHOD FOR LOW INTENSITY OPTICAL HAIR GROWTH CONTROL

(75) Inventors: Michiel Errit Roersma, Eindhoven (NL); Antonius Maarten Nuijs, Eindhoven (NL); Francesco Roosen, Amsterdam (NL); Paul Anton Josef Ackermans, Nuenen (NL); Rieko Verhagen, Vught (NL); Gerhardus Wilhelmus Lucassen, Eindhoven (NL); Johannes Johanna Van Herk, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1209 days.

(21) Appl. No.: 12/433,135

(22) Filed: Apr. 30, 2009

(65) Prior Publication Data

US 2009/0210037 A1 Aug. 20, 2009

Related U.S. Application Data

(63) Continuation of application No. 11/165,987, filed on Jun. 24, 2005, which is a continuation-in-part of (Continued)

(51) Int. Cl.
*A61N 5/06* (2006.01)

(52) U.S. Cl.
CPC .................... *A61N 5/0617* (2013.01)

(58) Field of Classification Search
CPC ............... A61B 18/20; A61B 2018/20; A61B 2018/00452; A61B 2018/00476
(Continued)

(56) References Cited

U.S. PATENT DOCUMENTS 5,059,192 A 10/1991 Zaias
5,885,273 A 3/1999 Eckhouse
(Continued)

FOREIGN PATENT DOCUMENTS

EP 0736308 A2 10/1996
JP 3066387 A1 3/1991
(Continued)

OTHER PUBLICATIONS

J.Lepselter et al; "Biological and Clinical Aspects in Laser Hair Removal", Apr. 2004, Journal of Dermatological Treatment, vol. 15, pp. 72-83.
(Continued)

*Primary Examiner* — Lynsey C Eiseman

(57) ABSTRACT

The present invention discloses a device and a method for controlling growth of hair on human skin with low doses of electromagnetic radiation, and a device for carrying out the method. In the method, radiation of a suitable spectrum is applied to the skin, in one or more pulses of between 1 and 100 ms, and with maximum fluencies on the skin between 1 and 12 J/cm2. By applying such low fluencies and at controlled pulse durations, follicles of the hairs are induced to the catagen phase. This means that the growth of the hairs of those follicles will stop. Although the method is not primarily aimed at immediate hair removal, hairs may be shed subsequently. In any case, further growth may be stopped for prolonged periods of time. The main advantage of the method is that the risk of damage to the skin is minimized.

10 Claims, 2 Drawing Sheets

Figure 1:
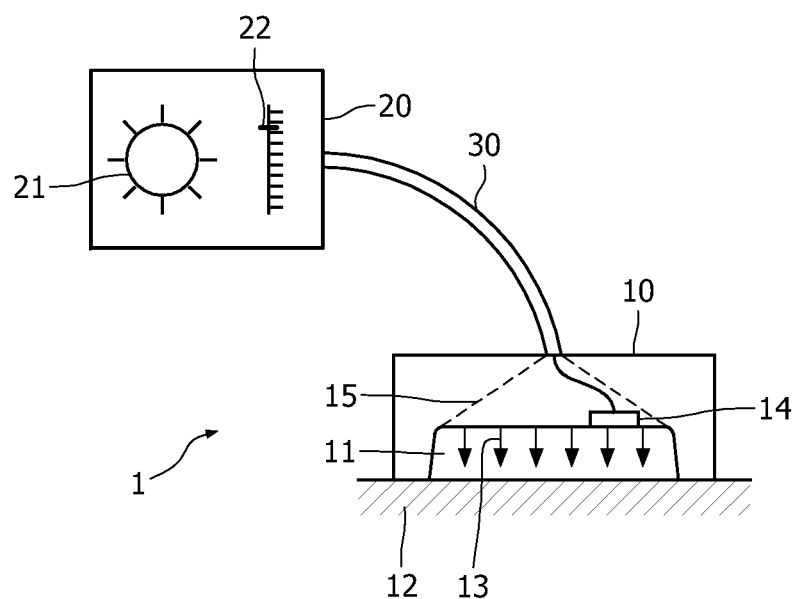

Related U.S. Application Data application No. 10/568,473, filed on Feb. 15, 2006, now Pat. No. 9,132,279.

(58) Field of Classification Search
USPC .............................................................. 606/9
See application file for complete search history.

(56) References Cited

U.S. PATENT DOCUMENTS

| | | | |
|---|---|---|---|
| 6,080,146 | A | 6/2000 | Altshuler |
| 6,080,147 | A * | 6/2000 | Tobinick .............. A61B 18/203 606/10 |
| 6,168,589 | B1 * | 1/2001 | Tobinick .......................... 606/9 |
| 6,235,015 | B1 | 5/2001 | Mead et al. |
| 6,273,884 | B1 | 8/2001 | Altshuler |
| 6,579,283 | B1 | 6/2003 | Tobinick |
| 6,595,985 | B1 * | 7/2003 | Tobinick .......................... 606/9 |
| 7,066,929 | B1 * | 6/2006 | Azar et al. ........................ 606/9 |
| 2002/0045891 | A1 * | 4/2002 | Clement .............. A61B 18/203 606/9 |
| 2002/0049432 | A1 * | 4/2002 | Mukai .................. A61B 18/203 606/9 |
| 2002/0173782 | A1 | 11/2002 | Cense et al. |
| 2003/0032950 | A1 * | 2/2003 | Altshuler et al. ................ 606/9 |
| 2004/0034319 | A1 * | 2/2004 | Anderson et al. ............. 604/20 |
| 2004/0082940 | A1 * | 4/2004 | Black .................. A61B 18/203 606/9 |
| 2004/0092918 | A1 * | 5/2004 | Jay ....................... A61B 18/203 606/9 |
| 2006/0247740 | A1 | 11/2006 | Roersma et al. |

FOREIGN PATENT DOCUMENTS

| | | |
|---|---|---|
| JP | H0366387 A | 3/1991 |
| WO | 9728752 A1 | 8/1997 |
| WO | 9824507 A2 | 6/1998 |
| WO | 99432264 A1 | 9/1999 |
| WO | 03077783 A1 | 9/2003 |
| WO | 2005016453 A1 | 2/2005 |

OTHER PUBLICATIONS

Elise A. Olsen, "Methods of Hair Removal", Journal of the American Academy of Dermatology, vol. 40, Issue 2, Feb. 1999, pp. 143-155.

Richard J. Ort, R. Rox Anderson, "Optical Hair Removal", Seminars in Cutaneous Medicine and Surgery, vol. 18, Issue 2, Jun. 1999, pp. 149-158.

Richard J. Ort, Christine Dierickx, "Laser Hair Removal", Seminars in Cutaneous Medicine and Surgery, vol. 21, Issue 2, Jun. 2002, pp. 129-144.

R.A. Weiss, Weiss, M.A., Marwaha S. Harrington A.C., "Hair Removal With a Non Coherent Filtered Flashlamp Intense Pulsed Light Source", Lasers Surg Med 1999; 24(2). Hairfacts. http://hairfacts.com/medpubs/flashlmp/weiss.html, pp. 1-2.

* cited by examiner

DEVICE AND METHOD FOR LOW INTENSITY OPTICAL HAIR GROWTH CONTROL

CROSS REFERENCE TO RELATION APPLICATION

This application claims the benefit or priority of and describes the relationships between the following applications: wherein this is a Continuation of U.S. patent application Ser. No. 11/165,987, filed Jun. 24, 2005, which is a continuation-in-part of U.S. patent application Ser. No. 10/568,473, filed Feb. 15, 2006, which is a 371 of international application PCT/IB2004/051395, filed Aug. 5, 2004, and which claims foreign priority from EP03102582.8, filed on Aug. 18, 2003.

The present invention relates to a device for reducing growth of hairs on human skin, which device comprises a source of electromagnetic radiation that emits in a wavelength range between 550 and 1200 nm.

The invention also relates to a method for reducing growth of hairs on human skin, comprising delivering at least one pulse of electromagnetic radiation to the skin, wherein a wavelength spectrum of the electromagnetic radiation is selected between 550 and 1200 nm.

In the state of the art it is known to use electromagnetic radiation to remove hairs from the human skin. This is called photoepilation. Almost all of the known methods and apparatus obtain photoepilation by delivering an amount of energy to the follicles of the hairs which is sufficient to induce permanent damage to the follicles. This damage may be caused either by heating the follicles, or at least radiation absorbing particles in or near the follicles, e.g. chromophores such as melanin, to a sufficient temperature, or by providing a power density which is sufficient for such particles to explode and inflict mechanical damage on the follicles. This damage to the follicles will cause the hairs to be shed, within a short time after the treatment. Hair regrowth may be prevented for a prolonged period of time.

However, these known methods of photoepilation are rather painful, and may cause skin burns and other side effects, and inherently damage tissue in that follicles are to be damaged. A main reason therefor is the use of high energy densities of up to 40 J/cm2 at the surface of the skin. Hence methods have been proposed with a lower energy load on the skin, which would therefore be less painful.

WO-98/24507 proposes a two-step method to remove hair, comprising a first step to induce synchronized growth of hairs, which is to be followed by a second step of other hair removal procedures. Firstly, hairs are synchronized in the late telogen phase/early anagen phase by irritating or slightly damaging the hair follicles so as to stimulate hairs in the skin section that are in the catagen or telogen phase to shift to the anagen phase of the hair growth cycle. The irritation or damage must not be sufficient to cause hair follicles in the anagen phase to be shifted to an inactive state. Alternatively, a radiation treatment can be used to shock anagen phase hair follicles into the telogen phase while stimulating the resting cells to transition into the anagen phase, thus synchronizing the hair cell growth. The goal of this treatment is to bring the hair follicles from an inactive into an active growth phase, while they are still in a shallow position in the skin, at a depth of about 1-2 mm, which differs from the 3-5 mm in the mature anagen phase. All this makes the follicles more vulnerable to a subsequent normal photoepilation treatment.

A disadvantage of the known method is that short pulses, in particular laser pulses, are supplied. Nothing more specific is said, but short pulses entail the risk of supplying a too high power density of radiation energy. Furthermore, the known method is to be followed by a second step of the factual hair removal, the preferred method being photoepilation. Hence the skin will subsequently be subjected to even more radiation, which may cause even more damage to tissue. Another disadvantage of the known method is that a person being treated has to wait a period of time after the synchronizing step, in order for the phase shift in the growth cycle to occur and to make the subsequent treatment more efficient.

This waiting period is between 3 and 25 days. This means that the complete two-step treatment will take at least said 3 days, i.e. it can never be performed in one day, at one sitting.

WO-A-03/077783 discloses a method and apparatus for hair growth management by applying a relatively low dose of optical radiation energy to a treatment area of a patient's skin. The energy dose is sufficient to at least traumatize a matrix portion of each follicle being treated, but not to cause either necrosis of most of each said follicle or immediate gross alteration of any hair shaft therein. The treatments are preferably performed a plurality of times at selected time intervals to achieve a desired level of temporary hair growth reduction. A disadvantage of this known method and apparatus is that the method and apparatus are not sufficiently effective over their entire parameter ranges.

An object of the present invention is to provide a device and a method for reducing growth of hairs on human skin of the kinds mentioned in the opening paragraphs, which are safe and efficient, which cause as little damage to skin tissue as possible, and by which the envisaged treatment of the skin can be performed by means of only one type of treatment.

In order to achieve this object, a device for reducing growth of hairs on human skin in accordance with the invention is characterized in that the device comprises control means for limiting the deliverable energy density of the radiation on the skin to a maximum value between 1 and 12 J/cm2.

In order to achieve this object, a method for reducing growth of hairs on human skin in accordance with the invention is characterized in that the energy density of the electromagnetic radiation delivered to the skin is selected to be between 1 and 12 J/cm, preferably between 5 and 9 J/cm2, wherein the duration of the pulse is between 1 and 100 ms, preferably between 1 and 30 ms, such that anagen follicles of said hairs are induced to a resting phase in their growth cycle, thereby substantially preventing permanent damage to follicles of the hairs.

With the device and method according to the invention, use is made of the insight that it is advantageous to stimulate the anagen hair follicles to switch to a telogen, or resting phase, or inactive phase. It was found that an appropriate combination of pulse time and low energy densities of the radiation may bring about said transition to the resting phase, in order to thereby control hair growth on the skin and obtain an efficient degree of temporary hair growth reduction. Moreover, because of the selected combination of pulse time and low energy densities, pain and other discomfort to the person being treated is minimal. In particular the chance of tissue being damaged is reduced to a minimum.

Although it is not a principal aim of the present invention to remove the hairs at once by applying the method, it may in fact have this result. This will be elucidated further hereinbelow. The main consideration is that hairs of a person that no longer grow will limit discomfort to the person, especially perceptual/cosmetic discomfort, i.e. limit the displeasing appearance of hairy skin, as well as an unwanted rough skin. If treated soon enough, the person will experience no or only very little discomfort from said hairs.

A particular embodiment of a device according to the invention is characterized in that, during operation, the control means limits the deliverable energy density of the radiation on the skin to a maximum value between 5 and 9 J/cm2. A high efficiency is obtained, while the risks of tissue damage are still kept low.

A particular embodiment of a device according to the invention is characterized in that, during operation, the control means selects the maximum value in accordance with selected properties of the skin to be treated. Said selected properties may be skin color and color of the hairs to be treated. This offers the advantage of achieving maximum efficiency with minimum risk of tissue damage. Said maximum value of the energy density delivered to the skin may be adjustable, for instance by a dermatologist, who may assess whether for example the color of the skin of a person being treated has changed (such as is caused by tanning). Furthermore, said maximum value may be selectable from a number of preset values, in order to allow the device to be used by or for persons with different requirements. A maximum value selection knob may be provided for that purpose.

For example, for a person with dark hairs but a light-colored skin, a higher energy density may be selected than in the case of a dark skin and pale hairs.

A particular embodiment of a device according to the invention is characterized in that the wavelength range is between 600 and 950 nm. A particular embodiment of a method according to the invention is characterized in that the wavelength spectrum is between 600 and 950 nm. For these wavelengths, there is a good absorption by elements of the follicle to be stimulated, such as melanin bodies. Advantageously, the wavelength range is adapted to the skin type and hair color of the person being treated.

Different skin types may need a different approach. For instance, it is preferable to use longer wavelengths, such as short wave infrared from about 800 to about 1200 nm, for persons with a dark skin, in order to prevent too much absorption by melanin in the skin, which is undesirable.

It is noted that the radiation may be continuous spectrum radiation, line spectrum radiation, monochromatic radiation, or a combination thereof. This also holds for the general range of 550-1200 nm. It must also be stressed that the actually emitted radiation may comprise other parts of the spectrum, but that it should emit at least in the indicated wavelength region.

Advantageously, in a device according to the invention the source is a pulsed source that emits radiation pulses with a duration between 1 and 100 ms. A particular embodiment of a device according to the invention is characterized in that the duration of the radiation pulses is between 1 and 30 ms. A preferred embodiment of a device according to the invention is characterized in that the duration of the radiation pulses is between 10 and 20 ms. A correct duration is important to prevent a too high power density in and on the skin, as a too high power density could cause tissue damage because of too quick or even violent heating of (parts of) tissue. A relatively long pulse duration limits the risk of tissue damage.

However, a too long pulse duration would limit the efficiency of the device. Good results are obtained with the preferred pulse duration, although other pulse durations are not to be excluded. With the preferred pulse duration the degree of thermal diffusion to the tissue surrounding the hair follicles is relatively low. As a result, most of the energy absorbed by the hair follicles will remain in the hair follicles, so that the absorbed energy is used as efficiently as possible in obtaining the desired effect of hair growth reduction, and the required energy density can be as small as possible.

In an advantageous embodiment of a device according to the invention, the pulse is obtained by moving a source of the electromagnetic radiation. This means that a certain area of the skin will be irradiated only during the time needed for a source of radiation, used in the device, to pass said area. This time is called the dwell time. This may be considered as one single pulse. Of course it is also possible to obtain a pulse by the controlled switching of a source of radiation. Likewise, more than one pulse may be generated.

In an even more advantageous embodiment of a device according to the invention, a velocity of the source and a power density of the radiation emitted by the source are selected such that the energy density of the radiation delivered to the skin is between 5 and 9 J/cm2. In this embodiment, the energy density of the radiation delivered to the skin is the mathematical product of the dwell time and the power density of the radiation emitted by the source. The selection of the velocity of the source will be made by the operator of the device, in accordance with instructions and with the selected power density of the source. It is to be understood that in this context 'source' means the part of a device that actually emits the radiation, whereas sometimes a distinction is made between the source as a part that generates the radiation and e.g. a treatment head that emits the radiation. It will always be clear what part is meant.

Preferably, the velocity of the source is measured, and the emitted power density is selected in dependence on said velocity, such that the energy density delivered to the skin is between 5 and 9 J/cm2. In this way it is ensured that the treated skin will not be overexposed to the radiation. The power density emitted by the source may be adapted to the actually selected velocity with which the source, or more precisely the treatment head, is being moved across the skin. Since this velocity will not always be constant, the power density emitted by the source also should not be constant, but adapted to the actual speed.

A particular embodiment of a device according to the invention is characterized in that the source is a continuous source, the control means being designed to measure a velocity with which the device is moved over the skin to be treated and to adjust the energy density of the radiation emitted by the source as a function of the measured velocity, such that the energy density of the radiation delivered to an area of the skin being treated is at most equal to the maximum value. Although it is not strictly necessary to measure said velocity, it will help in limiting the energy density emitted by the source to the maximum value. In particular, if the device is moved with a velocity v, and if an emission window of the device, that emits the radiation, has a dimension d in the direction of movement over the device, then a dwell time tD may be defined as tD=d/v. The dwell time is equal to the time during which an area of the skin is being irradiated. Assuming that the power density of the radiation emitted by the source has a constant value, both over the emission window and in time, then the energy density becomes equal to the mathematical product of said power density and said dwell time. The control means in this embodiment are designed to adapt the power density emitted by the source in order for the energy density to remain below the selected maximum value. To this end, the control means may, for example, comprise attenuation means, such as two adjustable polarizers, or they may be designed to adjust the power supplied to the source.

In particular, the control means comprise a velocity measuring means that is arranged for measuring a relative velocity of the device with respect to the area of the skin to be treated. The measurement result may be an aid in selecting a correct velocity of the device across the skin, e.g. by means of a look-up table. The velocity measuring means may be any known suitable device, such as wheels that contact the skin, or an optical device such as used in optical mouses.

Advantageously, the control means are arranged to vary the power of the source in dependence of the measured velocity. In this way the control means are able to counteract inevitable velocity variations while manually moving the device across the skin, by accordingly adapting the power output of the source. The device becomes much safer for private use, in that it is much easier to prevent a too high or too low dose to the skin tissue. Thus, efficient use without side effects or pain is achievable.

A special embodiment of the device of the type mentioned above further comprises a lens that is arranged for focusing the emitted radiation at a depth of between 1 and 4 mm, preferably about 2.5 mm, below the surface of the skin, when the device contacts the skin.

By using a focusing mechanism in the form of a lens, it is possible to separate the window size from the scan speed, thus enabling safe and easy private use with relatively low intensity radiation emitted from the window. This has the further advantage that the intensity in the skin layers between the device and the target are irradiated at a much lower intensity, thus decreasing possibly painful or harmful side effects.

It is noted that hair growth management in particular relates to preventing further growth of hairs by traumatizing, without killing, tissue that relates to the growth of the hair. In order to prevent pain and harmful side effects as much as possible, the dose and irradiation time should be as indicated, higher doses and/or different time periods easily giving rise to skin damage, pain etc.

In particular, the image of the source is provided at a depth of between 1 and 4 mm, preferably about 2.5 mm, below the surface of the skin, when the device contacts the skin. Thereto an appropriate lens and/or an appropriate distance of the source, and/or the lens, to the skin, is selected. Simple optical calculations suffice to determine optical lens power and distance. Note that when the image is inside the skin, the scattering properties of the skin prevent focusing to a point or line. It has been found that at a depth of about 2.5 mm, and at a wavelength of about 800 nm, the minimum width of the image is about 1.5 mm. At other depths and wavelengths, this minimum width may have a different, smaller or larger value.

At the depth of between 1 and 4 mm, and in particular around 2.5 mm, hair growth related tissue is present, in particular hair stem cells and matrix of the follicle. Traumatizing such tissue is highly effective in preventing further growth of the hair present, possibly in combination with shedding of said hair. Necrotizing is however prevented at the indicated energy levels.

In a special embodiment, the source has a linear optical power output of between about 30 W/cm and about 80 W/cm. With the insight that the output of the device is focused to a width of about 1.5 mm, independent of the size of the source in the other, perpendicular direction, it is now possible to select a linear power density of the source, such that the required scan speeds are feasible for the purpose of hair growth management according to the method used in this invention. Feasible scan speeds for humans being roughly between about 5 and 20 cm/s, and with a dose between about 4 and 12 J/cm$^2$ in a time frame between 1 and 30 ms, preferably between about 10 and 30 ms, this embodiment offers a very useful device for private use. Such sources with linear optical power densities between about 30 and 80 W/cm are commercially available in compact and relatively inexpensive form, e.g. as laser diode bars or high-power LEDs. Note that other power outputs are possible, e.g. for professional use.

In a particular embodiment, the source is one of a continuous source or a pulsed source with a pulse repetition rate of at least about 1 kHertz. When a continuous source is used, there is provided a continuous and smooth illumination of the skin and skin tissue, without much risk of uneven doses when the device is moved across the skin. A pulsed source in principle has the disadvantage of providing inhomogeneous doses across the area when the source is moved, due to discontinuous radiation and only partly overlapping images. If the pulse repetition rate is sufficiently high with respect to the shift per pulse of the image, a quasi-homogeneous dose is obtained. With practically feasible velocities of up to 20 cm/s for the device and thus the image, and a width of about 1.5 mm, a repetition rate of about 1 kHz or more suffices for at least 10 images to overlap. Nevertheless, a continuous source is preferred for the above reasons.

The device according to the invention may comprise a single source, which may comprise itself many light exit parts, such as a set of optical fibers or other waveguides, or an array of LEDs etc. This is however to be taken as an integral unit. In a particular embodiment, the source comprises a plurality of separate, mutually parallel radiation subsources, each providing a respective image. If desired, this may be used to treat a larger area in one go, or to provide a more homogeneous dose due to multiple images.

Advantageously, the images of the subsources substantially overlap in the skin. In effect this increases the local intensity, to e.g. a double value in the case of two identical sources and (overlapping) images. This further increases safety of the device, in that the difference between intensity at the window surface and the intensity in the skin is increased.

In a particular embodiment, the control means are arranged to vary the power of fewer than all of the plurality of subsources in dependence of the measured velocity, wherein the control means are arranged to keep the power of at least one subsource at a substantially constant level, when the device is in use. In this way a device is provided with a continuous "basic" output, selected for a predetermined minimum velocity of say 5 cm/s, while the output may be increased by adding the output of one or more controllable additional (sub)sources, e.g. if the increased velocity or a different skin type requires so. For example, a basic setting of 30 W/cm may be used for every skin type, with a kind of "booster" in the form of additional up to 50 W/cm for skin types I-IV. It is of course also possible to make all subsources controllable, and have them function at a certain minimum level in order to ensure homogeneity of the radiation.

In a special embodiment, the control means comprise warning means for warning a user of the device when the measured velocity is outside a predetermined velocity range, the warning means comprising at least one of a visual or audible signalling device. Such warning means are useful to warn the user in order to prevent possible skin damage, or against an inefficient treatment at too high velocities. The warning means may be a coloured LED that lights, or blinks, or the like.

It is also possible to equip the device with means, or control means, to switch off the source(s) if the fluence or dose would become too high, due to decreased velocity or the like.

A particular embodiment of a device according to the invention is characterized in that the source comprises a flash lamp. A flash lamp is a simple and small broad band source, that can be controlled very easily by setting released energy and/or flash time. In particular, such a flash lamp is much smaller and more convenient than a laser.

Furthermore, a laser is also subject to stringent regulations, which makes a laser less suitable to be used as a source by unskilled persons at home.

Further objects, features and advantages of the invention will be understood more clearly by reading the following description of preferred embodiments.

The device for reducing growth of hairs on human skin according to the invention may be embodied like a known apparatus, and further comprise appropriate control means. These control means may comprise a small computer or comparable means.

In particular, the device may comprise a source of electromagnetic radiation, such as a flash lamp or halogen lamp. In this case, the source may comprise a filter for filtering out unwanted radiation, such as ultraviolet radiation. The device may emit the generated radiation through an emission window, which may consist of an opening in the device, or may comprise a piece of transparent material. Preferably, the emission window is cooled, e.g. a cooled sapphire window.

The device may further comprise velocity measuring means for measuring the velocity with which the device, and notably the emission window, is moved across the skin.

The control means are then designed such that they can process the measured velocity in order to set the emitted power density to a value that allows the energy density that is received by the skin to remain below a predetermined maximum value.

The device, and in particular the control means, may further comprise selection means for selecting the maximum value, in accordance with certain biophysical properties of the skin, such as skin color. The selection means may comprise a control knob that may be moved along an indicator scale in order to set the device to the correct combination of skin properties that are indicated on the indicator scale.

Preferably, the device comprises a sensor for measuring the biophysical skin properties, such as skin color, such that the device may be set to such values of the maximum value of energy density, spectrum and/or pulse duration that give the best efficiency without inducing unwanted side-effects.

Advantageously, the device, and in particular the control means, are automated, such that the setting of the device will take place automatically after measuring the skin to be treated. This will reduce the number of errors in operating the device.

Even more advantageously, the apparatus has one fixed setting of the maximum value of energy density, spectrum and/or pulse duration. This limits the number of errors even further, in that only one kind of treatment is possible. Preferably, the fixed setting is set based on the client's wish. This setting may be fixed in the factory or by a dermatologist etc. This offers a fool-proof device which is still optimized for the specific client and his skin.

Such fixed setting may however also be used more generally for people with about the same skin type, e.g. fair skin, etc.

In the method in accordance with the invention, anagen hair follicles are induced to go to a resting stage in their growth cycle, in order to thereby limit (re)growth of hair during a prolonged time, however without causing severe damage to the follicle.

Hair follicles go through the so-called hair growth cycle. A first phase in this cycle is called the anagen (growing) phase, in which the follicle produces a hair. At the end of the anagen phase the follicle switches to the catagen (intermediate) phase, which is automatically followed by the telogen (resting) phase. At the end of the telogen phase, after some time, the follicle will automatically enter the anagen phase again.

By switching the hair follicles to catagen phase and subsequently to telogen phase, by applying electromagnetic radiation to the skin with the device in accordance with the invention and in accordance with the method according to the invention, long lasting hair growth control is obtained. Since hair follicles in the telogen phase will shed their hairs, it is even possible that the hairs are removed with the method. However, this is not always the case, and will often take some time.

If such hair growth control is not sufficient, the method according to the invention may preferably be combined with other methods of hair removal, however preferably with methods that do not use electromagnetic radiation, since that would lessen the advantages of the present invention. Advantageously, the method is combined with e.g. plucking, waxing, shaving or chemical removing of the hairs. An advantage of this combination is that in effect hairs are removed, while at the same time regrowth is inhibited for a prolonged period of time. Note that plucking alone may also switch hair follicles to the catagen and then telogen phase, but plucking does not result in more than about 50% of the follicles being switched to catagen. Hence regrowth is suppressed less.

Another advantage of combining the method according to the invention with other types of epilation without radiation is that it may be performed by untrained people at home, without much risk of injury or tissue damage, and still provide even better hair growth control.

In an example of the method according to the invention, a flash lamp treatment at 9 J/cm2 optical energy at skin level, 15 ms pulse duration, and 600-950 nm spectrum showed similar hair results after one treatment as a flash lamp treatment at 15 J/cm2.

However, the discomfort to the persons being treated was much less. Persons treated with the device using the former settings can only just feel that their skin is being treated (e.g. a warm sensation on their skin), whereas persons treated with the device using the latter settings indicate that this treatment is rather painful to their skin. Moreover, the skin treated at 9 J/cm2 has a lower chance of burns, blisters, hypopigmentation, hyperpigmentation, etc. than the skin treated at 15 J/cm2.

In some cases it may be that only a portion of the anagen hair follicles are induced to switch to the catagen phase, followed by the telogen phase as a result of the treatment. In this case it is beneficial to wait a certain period, e.g. 2 weeks, and then treat the same area of skin again. This should be repeated until the final result is reached. After these initial treatments, regular treatments, e.g. at 2 week intervals, are applied to maintain the hair removal result by inducing catagen, followed by telogen, to those hair follicles that have naturally switched from the telogen to the anagen phase since the last treatment and have started growing a new hair.

Using the described method (9 J/cm2, 600-950 nm, 15 ms) and treatment protocol (shave and photo-epilate the skin every 2 weeks), typical results that can be reached are: 10% hair reduction 2 weeks after 1 treatment, 60% hair reduction 2 weeks after 2 treatments, and 90% hair reduction 2 weeks after 3 treatments.

Figure 2:
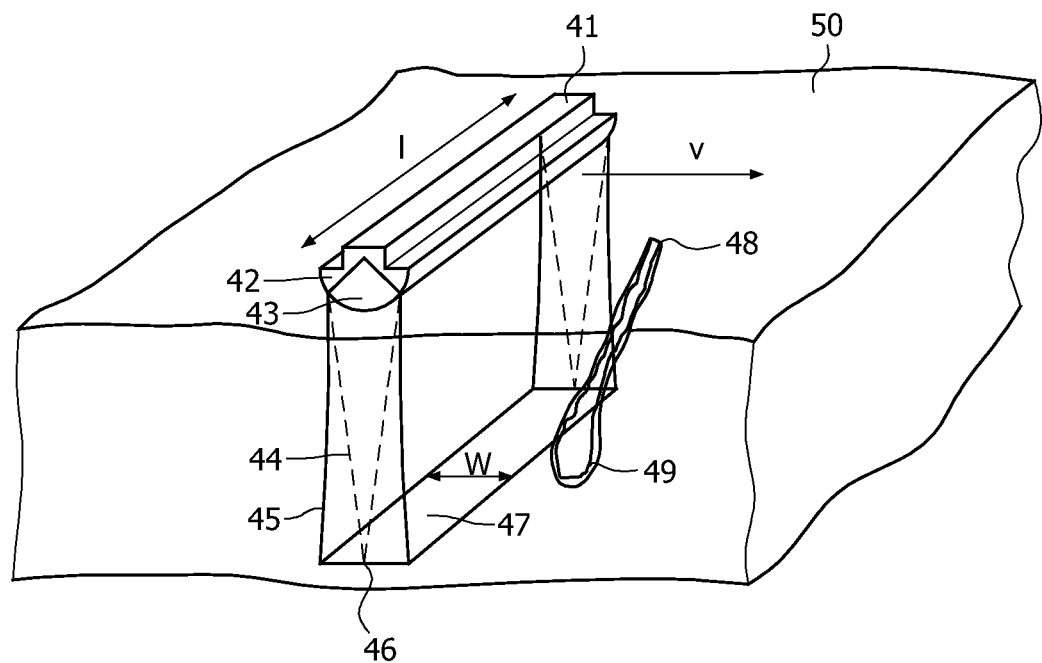
Figure 3:
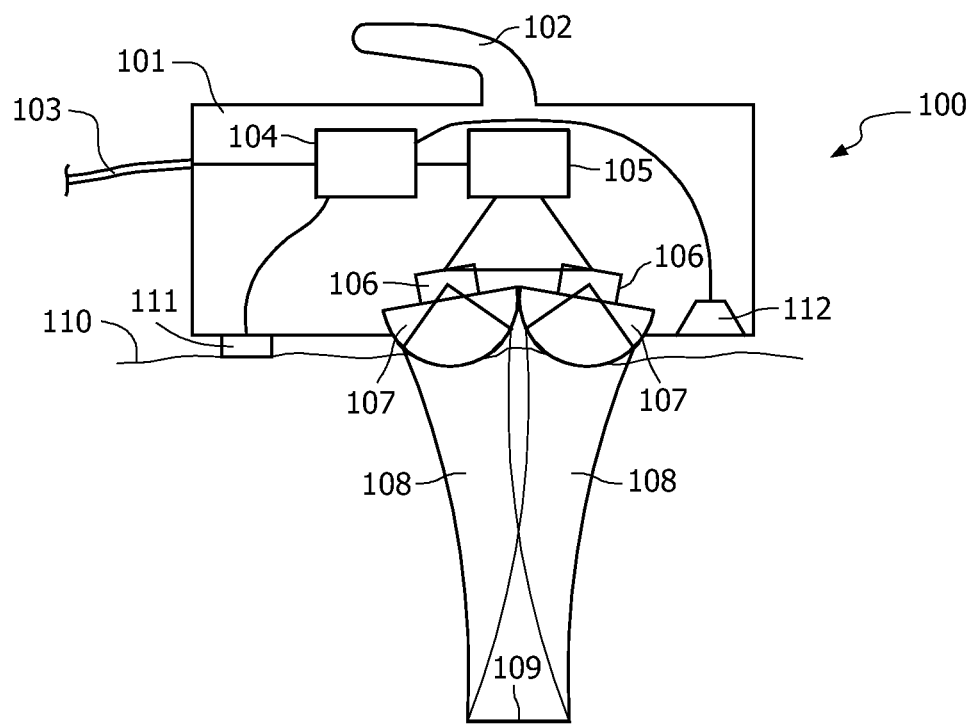

The present invention will be understood more clearly after reading the following description of a preferred embodiment, in connection with the appended drawing, in which FIG. 1 schematically shows a device for reducing growth of hairs on human skin according to the invention;

FIG. 2 diagrammatically shows another embodiment of the device according to the invention; and FIG. 3 diagrammatically shows a cross sectional view of a device according to the invention.

In the FIG. 1, the device 1 comprises a treatment head 10 and a power and control unit 20, interconnected by a connecting cable 30.

A treatment cavity is denoted by 11, and is to be placed on skin 12. 13 denotes radiation, and 14 is a sensor. Dashed line 15 indicates boundaries of radiation inside the treatment head.

The power and control unit comprises first and second control knobs 21,22 respectively.

The treatment head comprises a source (not shown) for the light 11. The source may either be present in the treatment head or outside it, e.g. in the power and control unit 20. In the latter case, the light may be transported through the connecting cable 30. The dashed lines 15 schematically indicate the boundaries of the lighting inside the treatment head 10. They may stand for the boundaries of a light bundle in the head 10, or e.g. for optical fibers that transport the light inside the head 10 towards the treatment cavity 11.

The light, or rather the radiation, that is used in the device may be any radiation according to the method of the invention. The wavelength is in the range of 550 to 1200 nm, for example yellow/red light. Suitable light sources are e.g. flash lamps, with filters, or a (pulsed) halogen lamp. The source may be powered and controlled by the power and control unit 20, although both functions may be separated if desired.

The treatment head 10 may be designed to cover an appropriate area of the skin 12. The treatment cavity 11 need not be a true cavity, but may also be covered with a transparent material, and it may also be completely absent in that the light is emitted from a surface in direct contact with the skin.

One advantage of there being a treatment cavity 11 is that a sensor 14 may be used for measuring biophysical properties of the skin 12. The sensor 14 measures for example the color and darkness of the skin 12, by analyzing the light reflected off the skin 12. The sensor 14 could also be used to determine a velocity of the treatment head 10, in order to determine the amount of released energy per skin area. However, it is also possible to use a separate sensor for one or more of these functions. Note that the sensor 14 is not at all indispensable in the device according to the invention.

The power and control unit 20 comprises first and second control knobs 21 and 22. Any other number of control knobs, such as one, three etc., and even zero, is also possible however. The latter indicates a preset device.

The first control knob 21 may be a power indicator, with which e.g. the maximum value of the energy density on the skin may be set. Typical values are for instance 4, 6 and 9 J/cm2, while a range between 1 and 12 J/cm2 is allowable according to the invention. The first control knob may also comprise, or be embodied as, an on-off function.

The second control knob may e.g. be a selector of the pulse time of the radiation used. Typical values for the pulse length according to the invention are between 1 and 100 ms, for instance 5, 10, 15, 20 and 30 ms.

Other possible controls include a selection of a specific spectrum by choosing an appropriate filter, or e.g. the selection of a certain user of the device. In the latter case, one knob may be used which sets all possible controls at once for the person which is to be treated. This option may for instance be useful in families, or in a dermatologist's practice.

Although the device 1 has been shown as made up of a separate treatment head 10 and power/control unit 20, it is also possible to integrate these into one unit.

However, a separate treatment head has the advantage that it may be smaller and more lightweight, which improves the operation of the device. The connecting cable 30 connects the treatment head 10 to the power and control unit 20. The connecting cable 30 may comprise a power cable for the treatment head, and an optional data cable for communication with e.g. the sensor 14. It is also possible that the source of radiation is built into the power and control unit 20, and that e.g. optical fibers are used to guide the radiation to the treatment head 10. In this case the optical fibers may also be comprised in the connecting cable 30.

The device 1 as shown may be combined with any other features that do not form part of the invention, but that may be useful, such as cooling surfaces, means for removing possible debris and smells, etc.

FIG. 2 diagrammatically shows another embodiment of the device according to the invention. Herein, 41 denotes a light source, 42 is a lens that focuses emitted light beam 43 into a focused non-scattered beam 44 with a focus 46. The actual focused and scattered beam 45 has a width w and projects a field 47. A hair 48 has a follicle 49 and is present in skin 50.

The light source 41 may be any desired light source as described above. In this embodiment, a diode laser bar is used, although e.g. a line or matrix of high-power LEDs etc. could also be used. A cylinder lens 42 focuses the light beam 43 that is emitted by the light source 41. In the absence of scattering, the focused light beam would be represented by beam 44. However, since skin is a scattering medium, the effective light beam would be the focused and scattered beam 45, which may be produced by the convolution of the non-scattered beam 44 with the point spread function that represent the scattering process. The effective width of the scattered beam 45 at the desired depth is denoted by w. This depth is determined by the depth of the tissue to be treated. As described above, a particularly preferred tissue is the matrix of the follicle 49 of the hair 48 in the skin 50. This depth is somewhat dependent on the anatomical region on the body, the type of hair to be treated and of the stage of development thereof, and varies roughly between 1 and 4 mm. By providing an adjustable lens system, this depth may be adjusted. However, it is also possible to use a fixed lens system, providing a fixed depth of e.g. 2.5 mm, which is a useful depth. Alternatively, it is possible to provide a depth adaptation system to the treatment device, in much the same way as with a trimmer or clippers.

The width w in the drawing has been exaggerated for clarity reasons. In reality, the width of the window, or lens in this case, is larger than that of the image w. This not only reduces the required scan speed, but also increases the achieved intensity at the desired depth in the skin without heating the overlaying skin layers unduly.

The width w depends on scattering, which in turn depends on wavelength. At around 800 nm the minimum width that can be obtained at a depth of about 2.5 mm below the skin surface is approximately 1.5 mm.

By passing the device with the light source 41 over the skin 50 with a velocity v as indicated by the arrow v in FIG. 2, the dwell time of illuminated field 47, hereinafter also referred to as the "image", as it passes by over a follicle bulb is given by td=w/v. If P/l is the linear optical power of the source with total power P and length l, the fluence per surface area that is delivered during the dwell time is given by F=P/vl. Since effective hair removal may be brought about by fluences F e.g. in the range of about 9-12 J/cm2, it follows that in that case v lies between 3.7 cm/s and 5 cm/s for a light source with a linear (optical) power of 40 W/cm. On the other hand, the preferred dwell time (or pulse duration) td of 1-30 ms in combination with a width w of 1.5 mm gives a preferred velocity between 5 cm/s and 150 cm/s. An optimum compromise between the two velocities, taking both fluence and dwell time into account, is about 5 cm/s for the specific optical power of 40 W/cm. It is of course possible to fulfil both requirements (or better both preferences) in a wider range, e.g. by increasing the linear power to e.g. about 80 W/cm or taking a longer pulse duration 1-60 ms. The latter would however lower efficacy, as the preferred range of pulse duration is 1-30 ms. Note furthermore that a velocity between about 5 and 10 cm/s corresponds to a practically feasible velocity, since much higher or lower velocities are difficult to obtain in a controllable and repeatable fashion by consumers, with about 20 cm/s being the limit of practicality.

Use of the system comprises moving the light source 41 across the skin 50 with the desired velocity v, which is calculated or set in accordance with the skin type. In use, the radiation in the illuminated field 47 is absorbed by melanin in or near the follicle of the hair, in particular of the matrix. Absorption of radiation increases the temperature, until the matrix cells are traumatised and the hair follicle 49 switches to catagen, followed by telogen. In this phase, hair growth stops, and the existing hair is shed and may be easily removed with any known method or device and without causing pain or other discomfort.

FIG. 3 diagrammatically shows a cross sectional view of another device 100 according to the invention. The device 100 comprises a house 101 with a handle 102 for handling the device 100. A power cable 103 connects the device to e.g. the mains or other electrical power source. 104 denotes a control unit, 105 denotes a power supply for the light sources 106. A lens is indicated by 107, projecting a light beam 108 and illuminating an image 109 in the skin 110. A velocity detector is schematically denoted by 111 while a skin type detector 112 is also present.

The house 101 may have any suitable dimensions, adapted for comfortably treating skin parts, such as armpits, legs etc. Handle 102 may have any appropriate shape for handling the device 100.

Power cord 103 is optional if the device 100 is provided with batteries or another internal power source. Alternatively, the light sources 106 are external light sources, such as a laser source, the light emitted by the light sources being transported to the device 100 by an optical waveguide, such as optical fibers. In that case, no power cord 103 is required, although a light guide would be required.

The light sources 106 may be any of the light sources described above, or alternatives. Examples are laser diode bars, LEDs, or, especially in the case of external light sources, any other light source emitting in a desired wavelength range of between 550 and 1100 nm, the light being transported by light guides towards lenses 107. The light sources 106 may be true continuous light sources, such as continuous wave lasers, LEDs etc. Alternatively, the light sources 107 may be pulsed light sources, although continuous emission has an advantage that less or no stepwise differences in fluence will occur in the skin. In the case of pulsed light sources, it is preferable to use a high repetition rate, since this lowers the effect of stepwise or discontinuous fluences. A repetition rate is high if it is ensured that at least about 10 pulses illuminate any spot of the image 109 at a feasible speed of maximum 20 cm/s. A repetition rate of 1 kHertz or higher would suffice.

It is possible to use a single light source 106 and corresponding lens 107. In the embodiment shown, two separate combinations of light source 106 and lens 107 are used, such that their images overlap in the skin, at the desired depth. It is also possible to use even more light sources 106, such as three or more light sources, increasing even further the difference between luminous intensity at window (or source) level and at target level. Note that each light source 106 may itself comprise a plurality of separate light emitting parts, e.g. in the case of laser diode bars or arrays of optical fibers. However, each assembly of light emitting parts that form an integral unit, such as a laser diode bar, is considered to be a single light source for the purpose of the present invention.

It is preferable for the light sources to emit light in a direction such that the images 109 thereof overlap at the desired depth of e.g. 2.5 mm. This ensures that said image receives the maximum dose, while surrounding tissue receives only very low levels of intensity. This increases selectivity of the device. To achieve such overlapping images 109, it is preferable for the multiple light sources to be positioned parallel with respect to each other and emitting under an appropriate angle with respect to each other.

In the embodiment shown in FIG. 3, the light sources 106 may each have an optical power of for example between 30 and 50 W/cm. Alternatively, one light source may have an optical power of 30 W/cm and the other of 50 W/cm, with other combinations of powers also possible, provided that the added (maximum) optical power is between about 60 and 100 W/cm. Laser diode bars having optical powers of between 30 and 50 W/cm are commercially available at a reasonable price.

It is further advantageous to provide controllable light sources, e.g. in that the control unit 104 controls the power supply 105 such that the power supply to the light sources 106 is controlled dependent of velocity of the device with respect to the skin 110 and/or dependent of the skin type of the skin 110, as determined by means of skin type detector 112. Dependent of the required power, the control unit 104 sets the optical power supplied to the light sources 106. This may be achieved in a substantially symmetrical fashion, supplying both light sources 106 with the same electrical power. Alternatively, it is possible to switch on one of the light sources 106 at a substantially constant, e.g. full, power as soon as the velocity as determined by velocity detector 111 exceeds a predetermined minimum value of e.g. around 5 cm/s. Depending on the actually achieved velocity, the control unit 104 may set the electrical power delivered to the other light source 106 by power source 105. In such case, it may be advantageous to provide a first power source with a constant electrical power corresponding to an optical power of 30 W/cm, while the other light source or light sources are supplied with an electrical power corresponding to an optical power that is dependent of the actual velocity and may lie between 0 and say 50 W/cm. The use of a constant but relatively low optical power improves the homogeneity that can be achieved with the device 100. Adapting the electrical power supplied to the other light source 106 having a variable electrical power ensures that over a relatively wide range of velocities the actually supplied optical power is within an effective range. In this case, the optical power varies between about 30 and 80 W/cm, and is useful for velocities between about 5 cm/s and about 13 cm/s. Of course, if the velocity falls below about 5 cm/s, the fluence delivered to the image 109 would exceed the predetermined limit, and the device will be switched off by the control unit 104.

Alternatively, instead varying the electrical power directly, that is on a varying but substantially continuous basis, it is also possible to supply the power in the form of the series of pulses, at pulse frequencies of at least e.g. 1 kHertz, but preferably above about 10 kHertz in order to achieve sufficient homogeneity. Variations in actually required electrical power, e.g. based on variations in actual velocity, are translated into variations in pulse width, such that the locally delivered power is dependent on the velocity at that position on the skin.

The velocity detector 111 may be any appropriate detector for detecting the velocity of the device 100 with respect to the skin 110. Examples are mechanical wheels, optical mouse systems etc. The velocity detector 111 may be coupled to the control unit 104. If the velocity detected by the velocity detector 111 differs from the appropriate velocity, it is advantageous if the control unit 104 indicates to the user of the device 100 that the velocity should be corrected. Such indication may be brought about by means of visual or audible signs.

The light sources 106 should emit with such optical power that the fluence in the image field 109 is preferably in the range of about 1-12 J/cm2. The pulse time, also referred to as dwell time in the case of continuous light sources, should preferably be in the range of 1-30 ms, preferably around 15 ms. Hair reduction efficacies of roughly 90% can be obtained without pain or side effects with these settings. Near perfect smoothness between successive applications may be obtained, in particular when successive applications are no further apart than about six weeks.

The present invention has been illustrated by means of preferred embodiments. However, the invention is not to be construed as limited thereby. The scope of the invention is determined by the appended claims.

The invention claimed is:

1. A device for reducing growth of hair on human skin, the device comprising:
   a source for emitting electromagnetic radiation in a wavelength range between 550 and 1200 nm;
   a treatment head including
      boundaries of the electromagnetic radiation, and
      a sensor configured to measure a biophysical property of the skin and a velocity with which the treatment head is moved during operation over the skin; and
   a controller coupled to the source and the sensor and configured to
      limit a deliverable energy density of the electromagnetic radiation on the skin to a maximum value between 5 and 9 J/cm$^2$ in accordance with the measured biophysical property, and
      wherein during operation the maximum value is selectable by the controller in accordance with the measured biophysical property of the skin, and the maximum value of the deliverable energy density is deliverable through operation of the controller in the form of one single pulse of electromagnetic radiation having a duration between 1 and 30 ms, and
   wherein the source comprises two or more sources for emitting electromagnetic radiation and the controller is configured to maintain the energy density of a first one of the two or more sources at a constant level and adjust the energy density of the electromagnetic radiation emitted by at least a second one of the two or more sources as a function of the measured velocity.

2. The device as in claim 1, wherein the controller is configured to further limit the maximum value in accordance with hair color to be treated.

3. The device as in claim 1, wherein the wavelength range is between 600 and 950 nm.

4. The device as in claim 1, wherein the duration of the electromagnetic radiation pulse is between 10 and 20 ms.

5. The device as in claim 1, wherein the pulse duration is a dwell time of the device over an area of the skin when the device is moved and the controller is configured to turn off the source if the measured velocity falls below a predetermined minimum velocity.

6. The device as in claim 1, wherein the electromagnetic radiation is provided by a pulsed source and the controller is configured to provide at least one of a visual and audible signaling if the measured velocity is outside a predetermined velocity range.

7. The device as in claim 6, wherein the source comprises a flash lamp.

8. The device as in claim 1, further comprising a plurality of lenses, each lens corresponding to one of the two or more sources, each lens directing a corresponding light beam that illuminates an image in skin to overlap with each other corresponding light beam at a predetermined depth of the skin.

9. The device as in claim 8, wherein the predetermined depth is between 2 mm and 3 mm.

10. The device as in claim 8, wherein the light sources of the two or more light sources are pulsed light sources.

* * * * *